United States Patent
Weingart et al.

(10) Patent No.: US 12,251,511 B2
(45) Date of Patent: Mar. 18, 2025

(54) RESUSCITATION SYSTEM

(71) Applicant: Engineered Medical Systems, Inc., Indianapolis, IN (US)

(72) Inventors: Scott Weingart, Setauket-East Setauket, NY (US); Bradley Allen Wheeler, Martinsville, IN (US); Kevin Michael Pac, Fishers, IN (US)

(73) Assignee: Engineered Medical Systems, Inc., Indianapolis, IN (US)

( * ) Notice: Subject to any disclaimer, the term of this patent is extended or adjusted under 35 U.S.C. 154(b) by 1045 days.

(21) Appl. No.: 17/186,544

(22) Filed: Feb. 26, 2021

(65) Prior Publication Data
US 2022/0273897 A1 Sep. 1, 2022

(51) Int. Cl.
*A61M 16/00* (2006.01)
*A61M 16/06* (2006.01)
*A61M 16/20* (2006.01)

(52) U.S. Cl.
CPC .... *A61M 16/0084* (2014.02); *A61M 16/0003* (2014.02); *A61M 16/06* (2013.01); *A61M 16/209* (2014.02); *A61M 2016/0027* (2013.01); *A61M 2202/0208* (2013.01)

(58) Field of Classification Search
CPC .......... A61M 16/0084; A61M 16/0078; A61M 16/208; A61M 16/209
See application file for complete search history.

(56) References Cited

U.S. PATENT DOCUMENTS

| | | | |
|---|---|---|---|
| 5,301,667 A | 4/1994 | McGrail et al. | |
| D635,675 S | 4/2011 | Thompson et al. | |
| 8,534,283 B2 | 9/2013 | Howe, Jr. et al. | |
| 9,132,253 B2 | 9/2015 | Lynn et al. | |
| D760,376 S | 6/2016 | Korneliussen et al. | |
| D779,071 S | 2/2017 | Warner, III | |
| 2001/0029950 A1 | 10/2001 | Haubeil | |
| 2007/0049841 A1 | 3/2007 | Lepel | |
| 2008/0087285 A1 | 4/2008 | Kuo | |
| 2012/0012111 A1* | 1/2012 | Howe, Jr. ......... | A61M 16/1055 128/205.12 |
| 2015/0096559 A1 | 4/2015 | Duval-Arnould et al. | |
| 2015/0238722 A1* | 8/2015 | Al-Ali ................ | A61M 16/085 128/205.13 |
| 2015/0352303 A1 | 12/2015 | Godwin | |
| 2016/0367781 A1 | 12/2016 | McCollum et al. | |
| 2017/0095631 A1* | 4/2017 | Fukunaga ........... | A61M 16/125 |
| 2017/0157348 A1* | 6/2017 | Gillespie .......... | A61M 16/0816 |
| 2018/0369526 A1 | 12/2018 | McGowan et al. | |

(Continued)

Primary Examiner — Margaret M Luarca
(74) Attorney, Agent, or Firm — Woodard, Emhardt, Henry, Reeves & Wagner, LLP (57) ABSTRACT

A resuscitation system including a device or kit adapted for connection to a gas outlet of a resuscitation bag with a first gas inlet thereto and upstream of a face mask, the device or kit providing gas flow in a path from the bag to the mask. A check valve is operably connected to the gas outlet of the resuscitation bag and substantially blocking gas flow upstream thereof and allowing gas flow downstream thereof. A first safety release valve operably located downstream of the resuscitation bag and operable to release gas from the gas flow path at a predetermined pressure differential between the path and ambient. The first safety release valve is located downstream of the check valve.

20 Claims, 6 Drawing Sheets

(56) References Cited

U.S. PATENT DOCUMENTS

2019/0328987 A1    10/2019  Takatori et al.
2020/0222648 A1     7/2020  Alberici et al.
2020/0345967 A1*   11/2020  Merrell .............. A61M 16/208
2022/0273897 A1     9/2022  Weingart et al.

* cited by examiner

Fig. 6 ions relate. One embodi-
RESUSCITATION SYSTEM

FIELD OF DISCLOSURE

The present disclosure relates in general to manual resuscitation systems, and more specifically deals with a bag valve mask for providing positive pressure ventilation to patients.

BACKGROUND

Bag valve mask systems are typically utilized in emergency situations to provide positive pressure ventilation to patients who are not breathing or not adequately breathing. Bag valve mask systems are typically hand-held devices manually operated by an individual, such as a medical professional. As is intuitive in the name, a bag valve mask includes a bag for compressing and decompressing. When compressing the bag air is forced toward the patient. When released the bag is able to fill with air again. A is bag valve mask system further includes a one-way valve located between the bag and the patient and a mask for channeling the air to the patient. Typically, an oxygen inlet is provided on the bag side of the one-way valve so that when the bag is compressed, oxygen is delivered to the patient's lungs.

Current bag valve mask systems provide oxygen on the bag side of the one way valve. This leads to a lot of the oxygen being diluted or wasted by the time the air reaches the patient. Therefore, it is desirable to develop a bag valve mask system that provides the patient with adequate oxygen.

Thus, there is a need for improvement in this field.

SUMMARY

The present disclosure relates in general to manual resuscitation systems, and specifically deals with a bag valve mask for providing positive pressure ventilation to patients. An exemplary embodiment of the present disclosure includes a resuscitation system comprising a device or kit adapted for connection to a gas outlet of a resuscitation bag with a first gas inlet thereto and upstream of a face mask. The device or kit provides gas flow in a path from the bag to the mask.

The system may include a check valve operably connected to the gas outlet of the resuscitation bag and substantially blocking gas flow upstream of the valve and back into the back and only allowing gas flow downstream of the valve toward the patient. The system may further include a first safety release valve operably located downstream of the resuscitation bag and operable to release gas from the gas flow path at a predetermined pressure differential between the path and ambient air. The first safety release valve may be located downstream of the check valve.

The resuscitation system may further include a second gas inlet. The second gas inlet may be operably located downstream of the resuscitation bag. Further, the second gas inlet can be located downstream of the check valve. The second gas inlet advantageously provides supplemental oxygen on the patient side of the one-way check valve.

The resuscitation system may further include a second safety release valve. The second safety release valve may be located upstream of the check valve and is operable to release gas from the gas flow path at a predetermined pressure differential between the path and the ambient air.

The resuscitation system may include a PEEP valve with a biological filter integrated within a housing of the PEEP valve. The biological filter prevents particles from the patient's exhaled breathe from entering the atmospheric air.

The resuscitation system may further include a selectively attachable and detachable pressure gauge for measuring the pressure downstream of the check valve.

The system also includes an oxygen source for providing enriched oxygen to the patient's lungs during operation of the system. The oxygen source may be accessed by a separate oxygen line or an integrated and internally routed line within the resuscitation system.

The resuscitation system may be surgically sterilized and contained within a sterile package. The sterile package may include at least one of the components of the resuscitation system. Any combination of the components may be included in the sterile package.

Further forms, objects, features, aspects, benefits, advantages, and embodiments of the present inventions will become apparent from a detailed description and drawings provided herewith.

DESCRIPTION OF THE SELECTED EMBODIMENTS

For the purpose of promoting an understanding of the principles of the inventions, reference will now be made to the embodiments illustrated in the drawings and specific language will be used to describe the same. It will nevertheless be understood that no limitation of the scope of the inventions is thereby intended. Any alterations and further modifications in the described embodiments, and any further applications of the principles of the inventions as described herein are contemplated as would normally occur to one skilled in the art to which the inventions relate. One embodiment of the invention is shown in great detail, although it will be apparent to those skilled in the relevant art that some features that are not relevant to the present inventions may not be shown for the sake of clarity.

Figure 1:
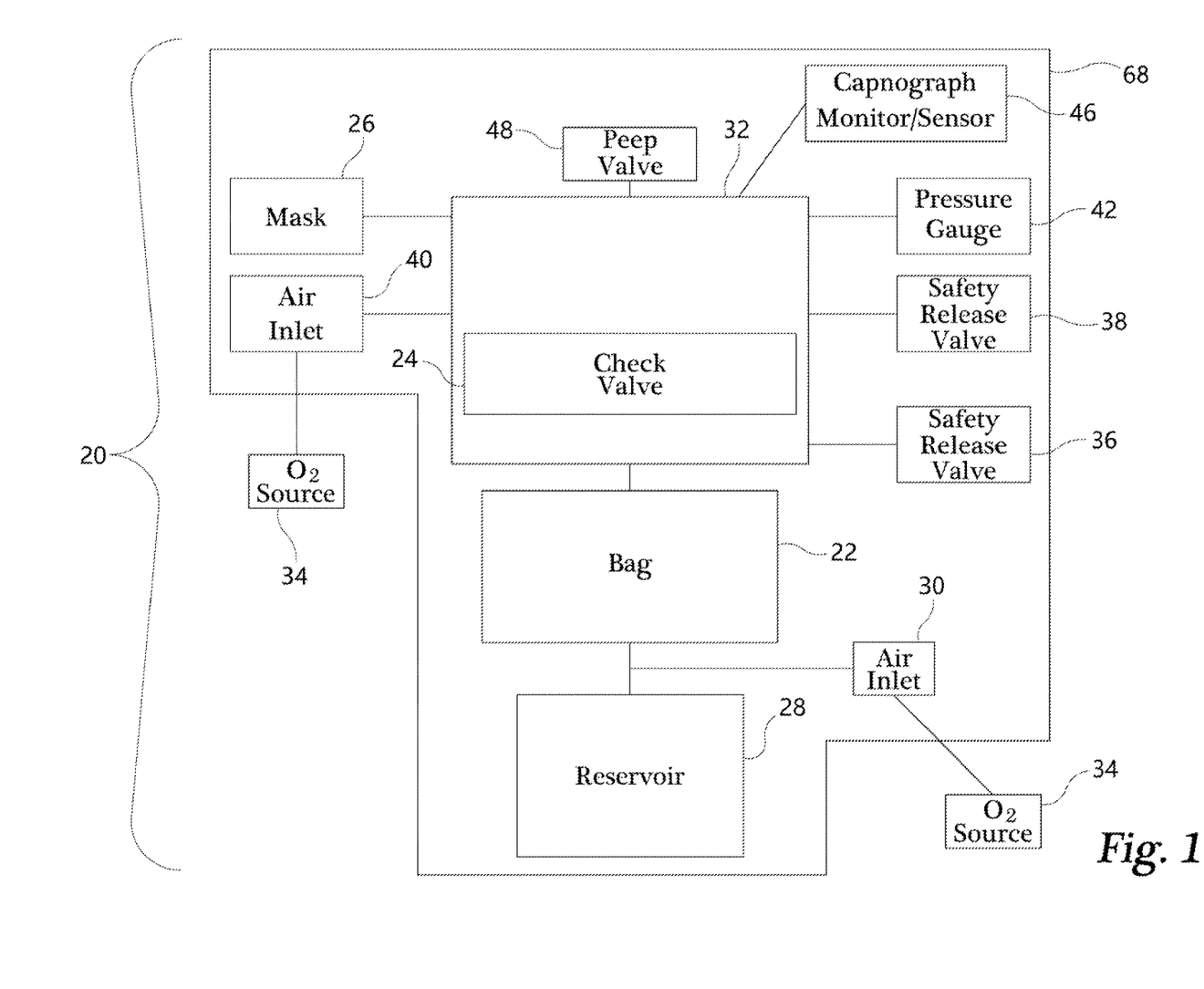
FIG. 1 is a schematic diagram view of a resuscitation system.

Referring to FIG. 1, there is illustrated a schematic view of a resuscitation system 20 or more specifically a bag valve mask system. As illustrated, the resuscitation system is a device or kit that may include a bag 22, check valve 24 and mask 26. The resuscitation system 20 defines a fluid flow path from the bag 20 to and out of the mask 26 to a patient's lungs. During use air travels along the fluid flow path from the bag out of the mask and to the patient. As described in further detail below, check valve 24 may be a one-way valve. The mask 26 may be any appropriate mask used in the prior art.

The resuscitation system 20 may further include a reservoir 28, air inlet 30 and valve housing 32. Air inlet 30 may connect and provide oxygen to the bag 22 and reservoir 28 from an oxygen source 34. The oxygen source 34 may be accessed by a separate oxygen line/tubing or by an integrated, internally route line/or tubing within the resuscitation system 20. The valve housing 32 may include a safety release valve 36 upstream of check valve 24 and a safety release valve 38 downstream of check valve 24. Both release valves 36, 38 may be integrated into the valve housing 32. The valve housing 32 may further include an air inlet 40 integrated into the valve housing 32 downstream of the check valve 24. Optionally, one or more of a pressure gauge 42, a PEEP valve 48 and a capnograph monitor 46 may be selectively attachable and detachable from the valve housing 32. The PEEP valve, when present, is preferably downstream of said check valve 24 and releasing gas therethrough to ambient (atmosphere) at a pressure lower than said first predetermined pressure of said first safety release valve.

Figure 2:
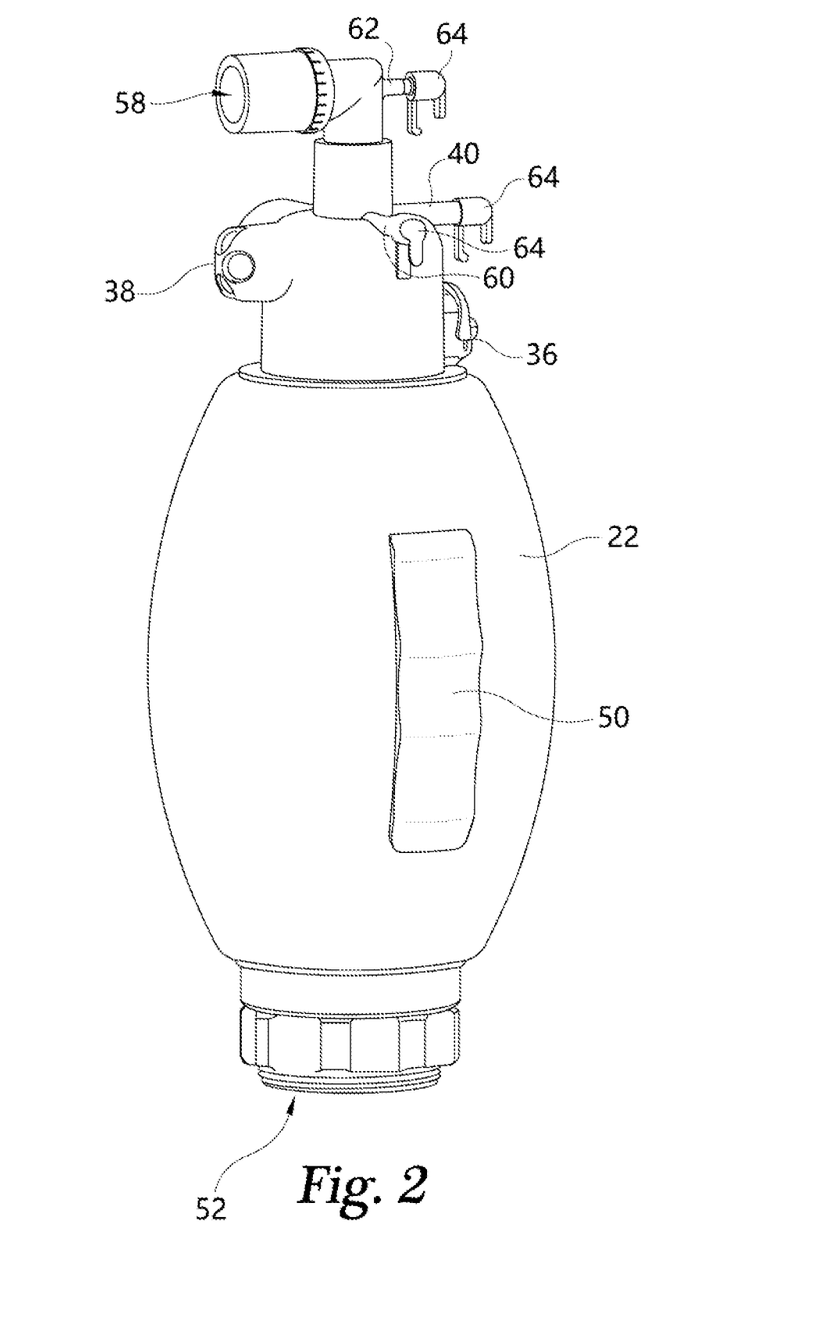
FIG. 2 is a side elevation view of the resuscitation system without a mask or reservoir.
Figure 3:
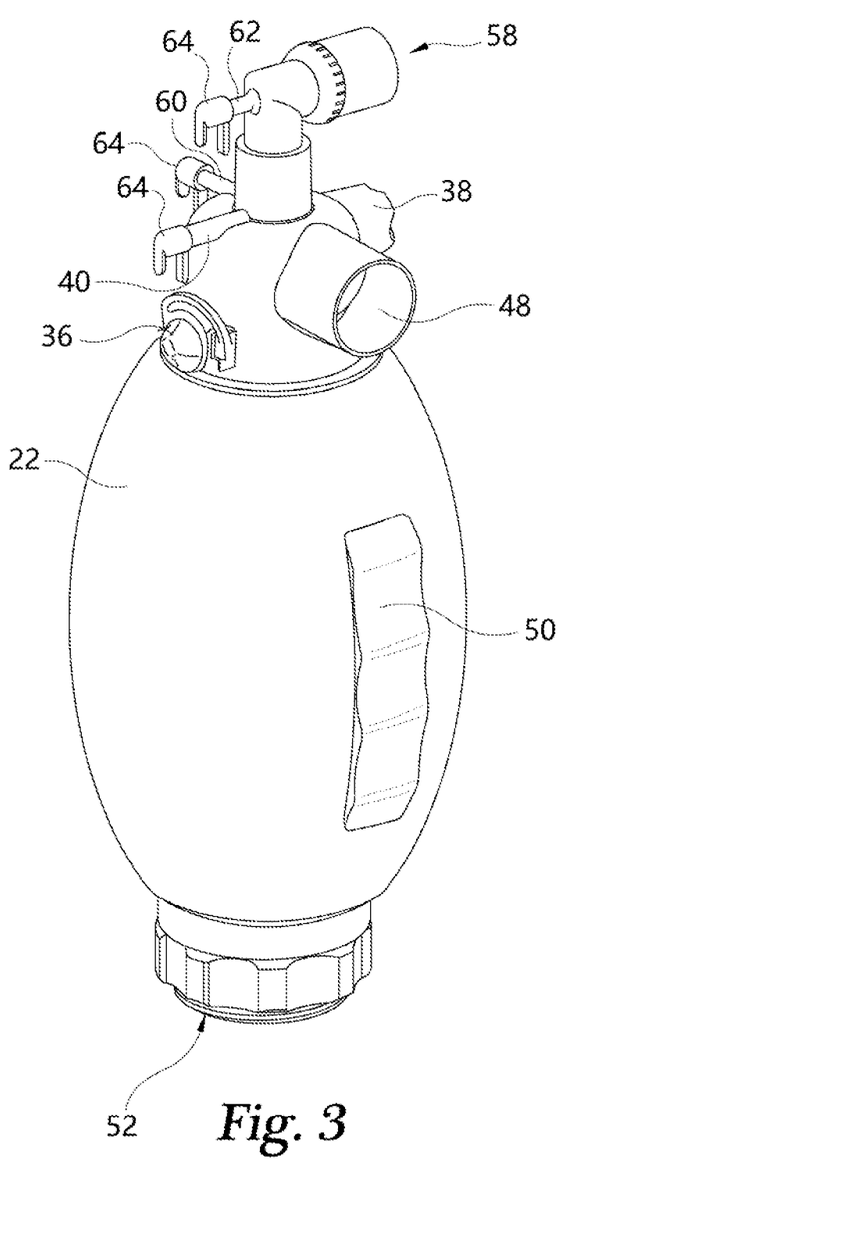
FIG. 3 is an additional side elevation view of the resuscitation system without the mask or reservoir.
Figure 5:
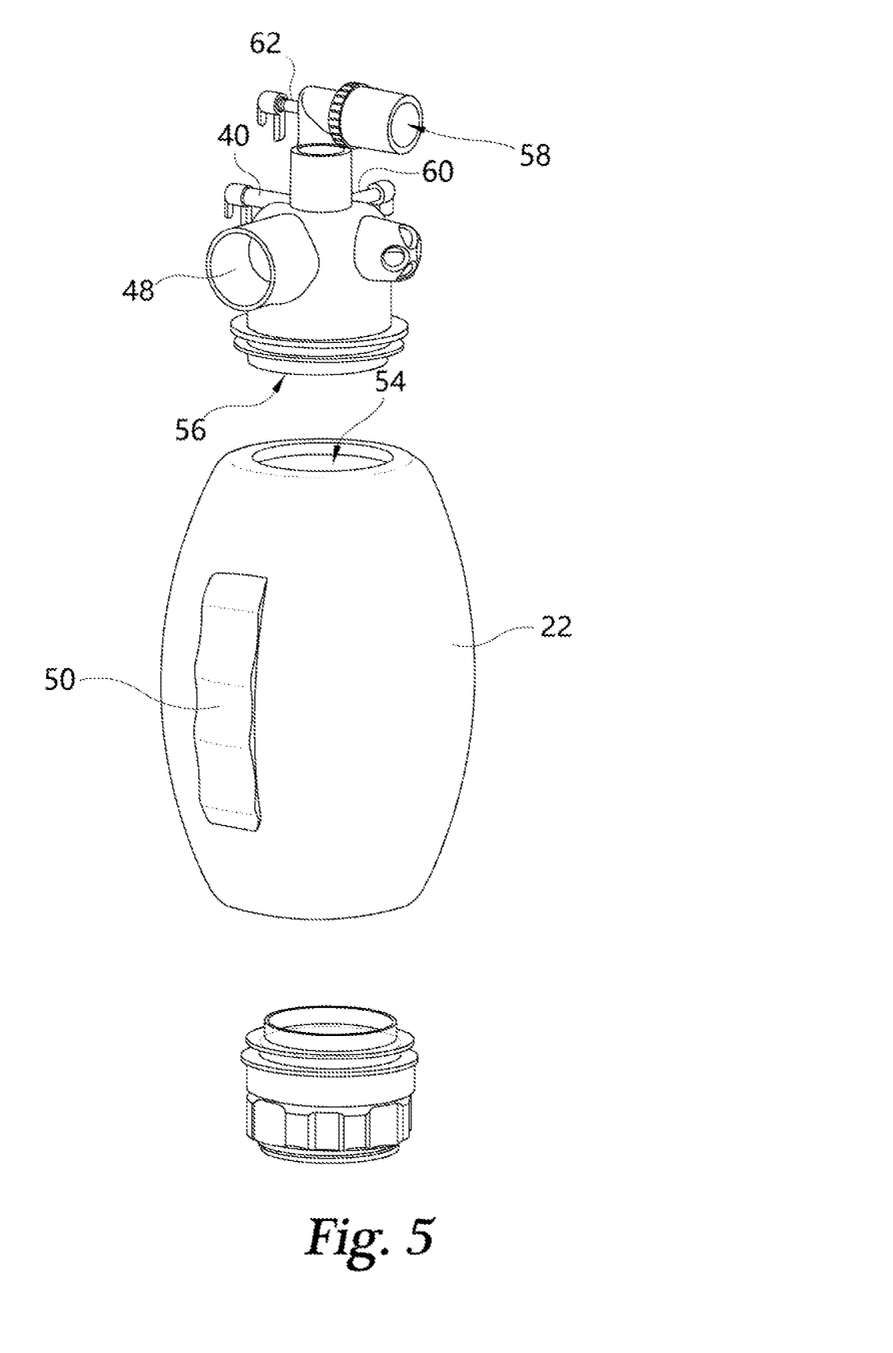
FIG. 5 is a partially exploded view of the resuscitation system without the mask or reservoir.
Figure 6:
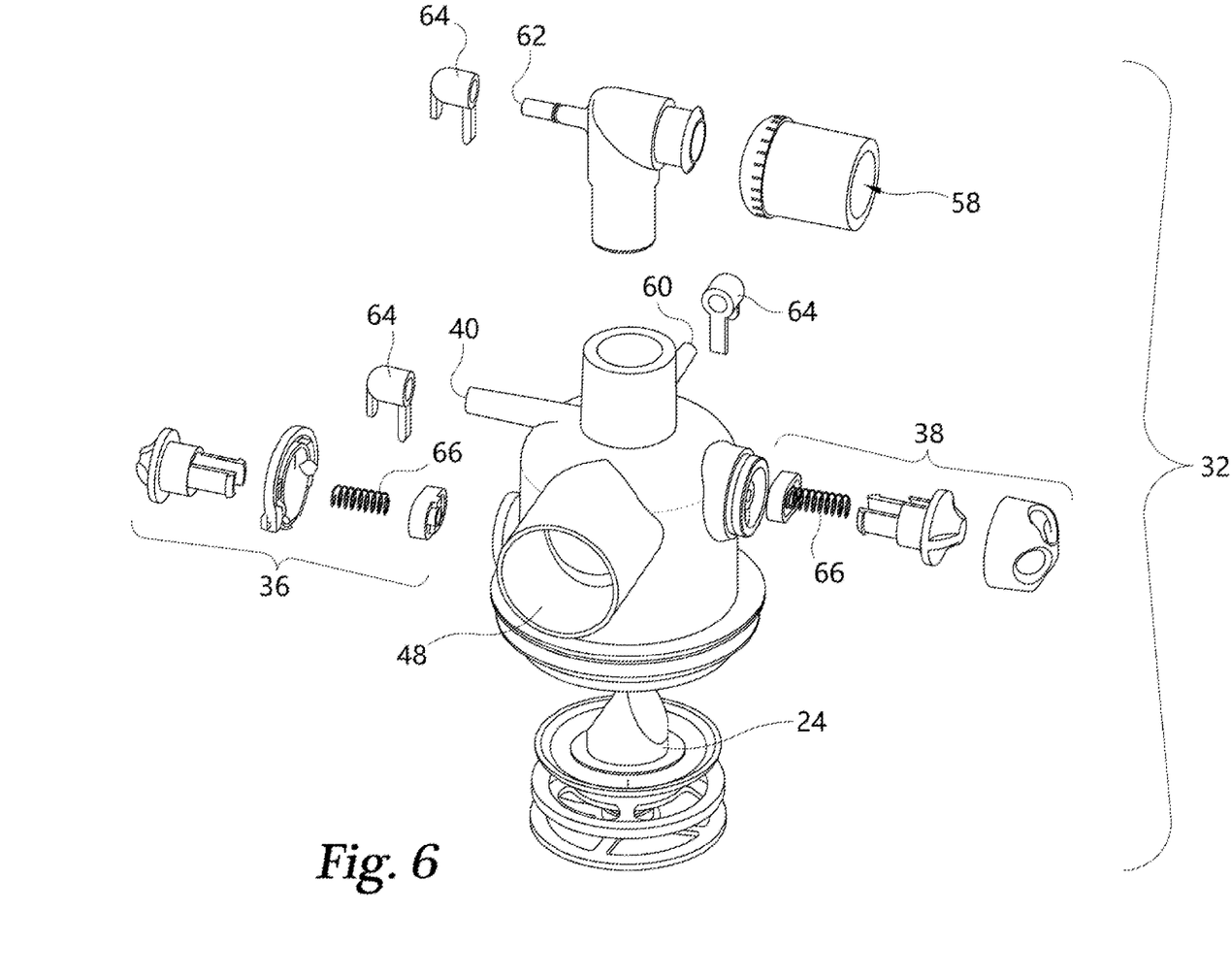
FIG. 6 is an exploded view of the valve housing.

FIGS. 2-3 and 5 illustrate two side elevation views of the resuscitation system. Bag 22 may be in the general shape of a football or a prolate spheroid and has an inner cavity to contain oxygen and/or air. Bag 22 may be formed from any suitable material, for example, silicone or rubber. Bag 22 may include grips or grooves 50 to help facilitate proper use of the bag. Grips 50 may be formed as an integrated part of the bag 22 or attached as separate pieces to the bag 22. In some embodiments, more than one grip 50 may be used to make it easier for right-hand or left-hand dominate users to grip and compress the bag 22. Bag 22 may further include gas inlet 52 for passing gas into the bag 22. Bag 22 may engage a reservoir 28 at gas inlet 52.

In some embodiments, the reservoir 28 may be a bag reservoir or corrugated tubing that attaches to an independent oxygen source 34. Bag 22 may also include a gas outlet 54. Gas outlet 54 is an opening in the bag 22 allowing gas to pass through is the opening and out of the bag 22 to the valve housing 32.

Figure 4:
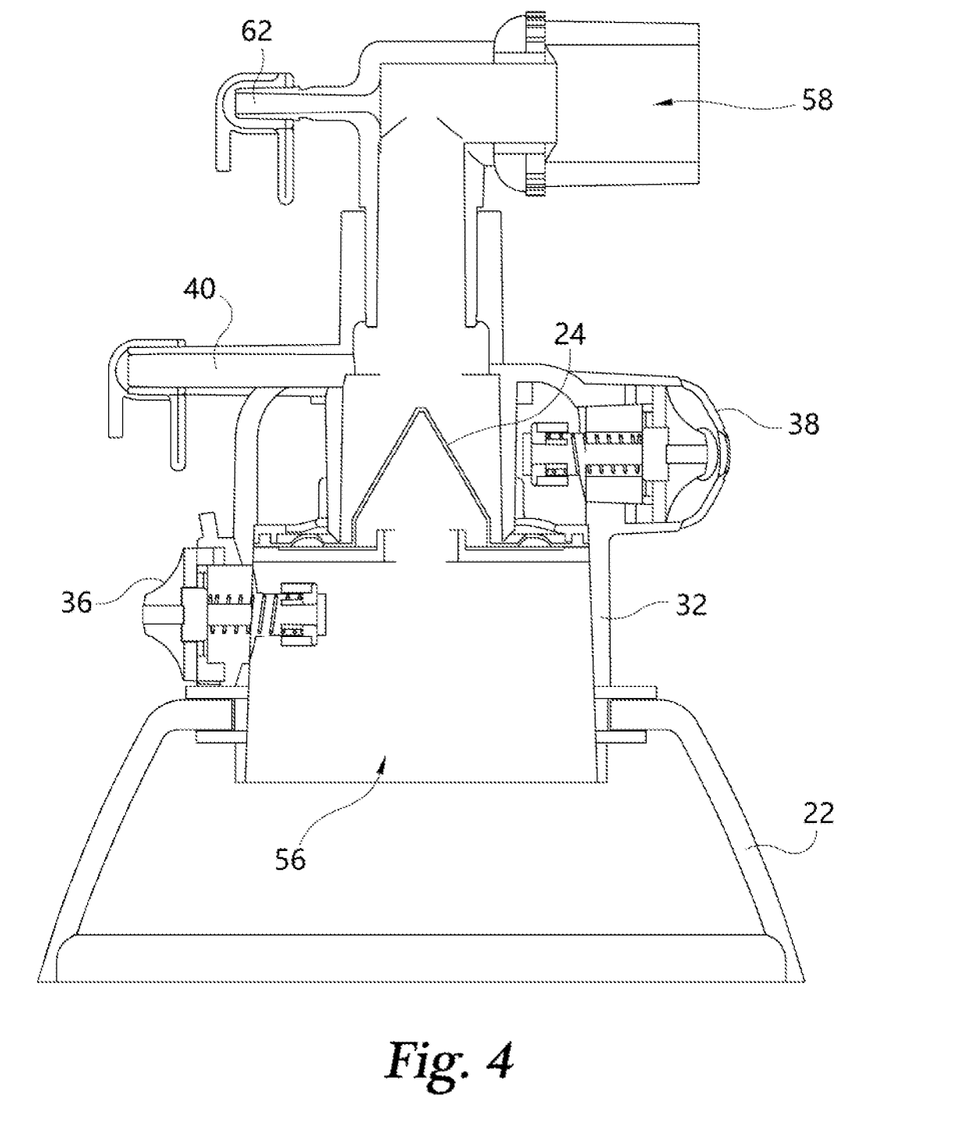
FIG. 4 is a cross-sectional view of a valve housing of the resuscitation system without the mask or reservoir.

FIG. 4, illustrates a cross-section view of the valve housing 32 and the check valve 24. Check valve 24 may be deposed along the fluid flow path of the resuscitation system within the valve housing 32. As illustrated the check valve 24 may be secured to the valve housing 32. In some embodiments, check valve 24 is a one-way valve. Check valve 24 allows air to travel downstream from the bag 22 through the mask 26 and to the patient. Because check valve 24 is a one-way valve, the air expelled by the patient cannot pass upstream through the valve and into the fluid path upstream of the check valve 24. This prevents the air upstream of the check valve 24 from being diluted or contaminated with undesirable particles such as carbon dioxide.

Referring to FIGS. 2-6, valve housing 30 may include a gas inlet 56 and a gas outlet 58. Both gas inlet 56 and gas outlet 58 are openings to allow the passing of gas in or out of the valve housing 32. Air passes through and out of gas outlet 54 of bag 22 and through gas inlet 56 into the valve housing 32 where the air may continue to pass downstream through check valve 24. After passing through the check valve 24, the air continues to travel through the valve housing 32 and out of gas outlet 58. In order to pass the air to the patient a mask 26 may be selectively attachable and detachable to gas outlet 58. The mask 26 may be any suitable mask known in the art.

Valve housing 32 may further include an integrated pressure gauge port 60. Pressure gauge port 60 may be located downstream of check valve 24. A pressure gauge 42, such as, a manometer may be selectively attached and detached from pressure gauge port 60. The pressure gauge 42 may be used to monitor the pressure during the patient's inhalation and exhalation.

Valve housing 32 may further include air inlet 40. Air inlet 40 may be located downstream or on the patient's side of valve 24. Air inlet 40 may be a supplemental oxygen port. Air inlet 40 may simply allow atmospheric air to enter through the open port and into the system. In other embodiments, supplemental oxygen sources 34 such as an oxygen tank may be connected to the air inlet by appropriate tubing to pump oxygen into the system. The oxygen source 34 may be the same source or an independent source from the oxygen source used for air inlet 30 This advantageously allows is supplemental oxygen to be provided on the downstream side of the check valve and to the patient during ventilation and increases pressure, ensuring that the patient is receiving as much oxygen as desired.

Valve housing 32 can also include capnography port 62 to monitor the concentration of carbon dioxide ($CO_2$) in the gases inhaled and exhaled by the patient. An air sampling tube may be connected to the capnography port to transport samples of air exhaled by the patient to be measured by a capnogram sensor/monitor 46.

The pressure gauge port 60, air inlet 40 and capnography port 62 may be covered by a cap 64 when not desired during use or during storage. This prevents unwanted entrainment of atmospheric air or contamination of the fluid path. The caps 64 may be easily removed to connect the various components described above.

Valve housing 32 may also include safety release valve 36 and safety release valve 38. Safety release valve 36 may be located upstream of check valve 24 and safety release valve 38 may be located downstream of check valve 24. Both safety release valves 36, 38 are biased by a spring 66 and may be manufactured or adjusted to release pressure at a predetermined pressure differential between the fluid path and the ambient air. Once the pressure in the resuscitation system 20 exceeds the predetermined pressure differential, the safety release valve 36, 38 is pushed open to release the pressure and maintain a safe level of pressure within the fluid path. Advantageously, this helps avoid over-pressurizing and damaging a patients lungs.

The components of the resuscitation system 20 may be surgically sterilized and contained within a sterile package/kit 68. The components (discussed above) may all come in one kit 68 or they may be sold separately. For example, one kit may include the check valve 24 and bag 22. Another kit 68 may include the mask 26. Yet another kit 68 may include the bag 22, valve 24 and mask 26. A PEEP Valve 48 or the tubing to connect the resuscitation system 20 to an oxygen source 34 may come in the same or separate kits 68. These examples are none limiting and any combination of the components discussed above may be included in the sterile packages 68.

A method for providing air to a patient using the fully assembled resuscitation system will now be described. During operation, the user may place the mask over a patient who is not breathing or having difficulty breathing. The user squeezes the bag to is force air downstream of the bag from the reservoir. The air passes through out of the gas outlet of the bag and into the valve housing through the gas inlet of the valve housing. Next, the air passes through the one-way valve. While open, the one way valve blocks the exhaust valve causing all the air to go into the patients lungs. The one-way valve then closes to prevent air from traveling upstream through the valve, such as during the patient's exhalation. If desired, supplemental oxygen may be added to the system by an air inlet downstream of the one-way valve to enrich the oxygen levels provided to the patient. A safety release valve downstream of the one-way valve may open, allowing an exit for the air before the pressure reaches an unsafe level and causes barotrauma of the lungs, such as during exhalation or from the increase in pressure provided by the supplemental oxygen. During ventilation, the user may monitor a number of factors, such as pressure and carbon dioxide levels.

Glossary of Terms

While examples of the inventions are illustrated in the drawings and described herein, this disclosure is to be considered as illustrative and not restrictive in character. The present disclosure is exemplary in nature and all changes, equivalents, and modifications that come within the spirit of the inventions are included. The detailed description is included herein to discuss aspects of the examples illustrated in the drawings for the purpose of promoting an understanding of the principles of the inventions. No limitation of the scope of the inventions is thereby intended. Any alterations and further modifications in the described examples, and any further applications of the principles described herein are contemplated as would normally occur to one skilled in the art to which the inventions relate. Some examples are disclosed in detail, however some features that may not be relevant may have been left out for the sake of clarity.

Where there are references to publications, patents, and patent applications cited herein, they are understood to be incorporated by reference as if each individual publication, patent, or patent application were specifically and individually indicated to be incorporated by reference and set forth in its entirety herein.

Singular forms "a", "an", "the", and the like include plural referents unless is expressly discussed otherwise. As an illustration, references to "a device" or "the device" include one or more of such devices and equivalents thereof.

Directional terms, such as "up", "down", "top" "bottom", "fore", "aft", "lateral", "longitudinal", "radial", "circumferential", etc., are used herein solely for the convenience of the reader in order to aid in the reader's understanding of the illustrated examples. The use of these directional terms does not in any manner limit the described, illustrated, and/or claimed features to a specific direction and/or orientation.

Multiple related items illustrated in the drawings with the same part number which are differentiated by a letter for separate individual instances, may be referred to generally by a distinguishable portion of the full name, and/or by the number alone. For example, if multiple "laterally extending elements" 90A, 90B, 90C, and 90D are illustrated in the drawings, the disclosure may refer to these as "laterally extending elements 90A-90D," or as "laterally extending elements 90," or by a distinguishable portion of the full name such as "elements 90".

The language used in the disclosure are presumed to have only their plain and ordinary meaning, except as explicitly defined below. The words used in the definitions included herein are to only have their plain and ordinary meaning. Such plain and ordinary meaning is inclusive of all consistent dictionary definitions from the most recently published Webster's and Random House dictionaries. As used herein, the following definitions apply to the following terms or to common variations thereof (e.g., singular/plural forms, past/present tenses, etc.):

"About" with reference to numerical values generally refers to plus or minus 10% of the stated value. For example, if the stated value is 4.375, then use of the term "about 4.375" generally means a range between 3.9375 and 4.8125.

"Ambient" is the surrounding atmosphere and its conditions. When a concrete pressure is needed for measurement and/or comparison purposes, it is measured at sea level.

"And/or" is inclusive here, meaning "and" as well as "or". For example, "P and/or Q" encompasses, P, Q, and P with Q; and, such "P and/or Q" may include other elements as well.

"Biological filter" generally refers to the filters known in the art that trap particles exhaled by the patient and keeps those particles from exiting into the atmosphere, including those used in face masks or filters traps.

"Check valve" as used herein means a valve that allows fluid (liquid or gas) to flow through the valve in only one direction. Types of check valves may include ball check valves, diaphragm check valves, swing check valve or titling disc check valves, flapper valve, stop-check valve, lift-check valve, in-line check valve, duckbill valve or pneumatic non-return valve.

"Downstream" as used herein means in the direction of the flow of air through the resuscitation system from the bag to the mask or toward the patient.

"Gas inlet" as used means an opening through which various gases may flow into a component or device.

"Gas outlet" as used means an opening through which various gases may flow out of a component or device.

"Multiple" as used herein is synonymous with the term "plurality" and refers to more than one, or by extension, two or more.

"Optionally" as used herein means discretionary; not required; possible, but not compulsory; left to personal choice.

"Oxygen source" as used herein the source of the oxygen being provided into the fluid flow path of the resuscitation system. For example, atmospheric air or oxygen is from an artificial source, such as an oxygen tank.

"Path" as used herein means the route of flow of air from the starting point through the resuscitation system to the patient.

"Positive End Expiratory Pressure Valve or PEEP Valve" as used herein means a valve generally used to maintain a predetermined pressure level in the lungs of a patient who is being ventilated with oxygen or air. Typical PEEP valves include a spring biased relief valve which remains closed and prevents the patient from exhaling until the pressure of the patient's exhalation gas exceeds the force of the spring after which the valve opens and the patient's exhalation gas is exhausted through an exit port on the PEEP valve and into the atmosphere.

"Pressure gauge" generally refers to an instrument for measuring the condition of a fluid (liquid or gas) that is specified by the force that fluid would exert, when at rest, on a unit area, such as pounds per square inch or newtons per square centimeter. One example of a pressure gauge is a manometer.

"Resuscitation bag" as used herein means a self-inflating bag that is compressible. A resuscitation bag may be used in a bag valve mask or resuscitation system to force air downstream of the bag to an individual who is not breathing adequately. A resuscitation bag may be operably connected to a reservoir bag and/or and oxygen source.

"Safety release valve" as used herein means a valve used to control or limit the pressure in the resuscitation system to avoid over-pressurization or barotrauma of the lungs. When a predetermined pressure differential between the resuscitation system and the ambient air is reached, the valve opens to relieve pressure within the resuscitation system. Safety release valve may be synonymous with pressure relief valve and pressure limiting valve.

"Substantially" generally refers to the degree by which a quantitative is representation may vary from a stated reference without resulting in an essential change of the basic function of the subject matter at issue. The term "substantially" is utilized herein to represent the inherent degree of uncertainty that may be attributed to any quantitative comparison, value, measurement, and/or other representation.

"Upstream" as used herein means in the direction opposite to the flow of air through the resuscitation system or, in other words, away from the patient.

The invention claimed is:

1. A resuscitation system comprising a device or kit adapted for connection to a gas outlet of a resuscitation bag with a first gas inlet thereto and upstream of a face mask, the device or kit providing gas flow in a path from the bag to the mask, comprising:
    a check valve operably connected to the gas outlet of the resuscitation bag and substantially blocking gas flow upstream and allowing gas flow downstream thereof;
    a first safety release valve operably located downstream of the resuscitation bag and operable to release gas from the gas flow path at a first predetermined pressure differential between the path and ambient;
    a second safety release valve operably located downstream of the resuscitation bag; and
    wherein the first safety release valve is located downstream of the check valve.

2. The resuscitation system of claim 1, further comprising:
    a second gas inlet.

3. The resuscitation system of claim 2, wherein the second gas inlet is operably located downstream of the resuscitation bag.

4. The resuscitation system of claim 2, wherein the second gas inlet is located downstream of the check valve.

5. The resuscitation system of claim 1, further comprising:
    a resuscitation bag.

6. The resuscitation system of claim 1, wherein the second safety release valve is located upstream of the check valve.

7. The resuscitation system of claim 1, further comprising:
    a PEEP valve downstream of said check valve and releasing gas therethrough to ambient at a pressure lower than said first predetermined pressure of said first safety release valve.

8. The resuscitation system of claim 7, wherein the PEEP valve includes a biological filter integrated within a housing of the PEEP valve.

9. The resuscitation system of claim 1, further comprising:
    a face mask operably connected downstream of the check valve.

10. The resuscitation system of claim 1, further comprising:
    a pressure gauge for measuring the pressure downstream of the check valve.

11. The resuscitation system of claim 1, further comprising:
    an oxygen source.

12. The resuscitation system of claim 11, wherein the oxygen source is accessed by a flow path independent from the resuscitation system.

13. The resuscitation system of claim 11, wherein the oxygen source is accessed by a flow path integrated and internally routed within the resuscitation system.

14. A kit for a resuscitation system comprising the device of claim 1 surgically sterilized and contained within a sterile package.

15. A kit for a resuscitation system comprising the device of claim 5 surgically sterilized and contained within a sterile package.

16. The kit of claim 14 and further comprising a mask surgically sterilized and contained within said sterile package.

17. The kit of claim 14 and further comprising a resuscitation bag surgically sterilized and contained within said sterile package.

18. The kit of claim 16 and further comprising a resuscitation bag surgically sterilized and contained within said sterile package.

19. A resuscitation system comprising a device or kit adapted for connection to a gas outlet of a resuscitation bag with a first gas inlet thereto and upstream of a face mask, the device or kit providing gas flow in a path from the bag to the mask, comprising:
    a check valve operably connected to the gas outlet of the resuscitation bag and substantially blocking gas flow upstream and allowing gas flow downstream thereof;
    a first safety release valve operably located downstream of the resuscitation bag and operable to release gas from the gas flow path at a first predetermined pressure differential between the path and ambient;
    a second safety release valve operably located downstream of the resuscitation bag; and
    wherein the first safety release valve is located downstream of the check valve, and wherein the second safety release valve is located upstream of the check valve.

20. A resuscitation system comprising a device or kit adapted for connection to a gas outlet of a resuscitation bag with a first gas inlet thereto and upstream of a face mask, the device or kit providing gas flow in a path from the bag to the mask, comprising:
    a valve housing adapted for connection to a gas outlet of a resuscitation bag;
    a check valve located within the valve housing and substantially blocking gas flow upstream and allowing gas flow downstream thereof;
    a first safety release valve connected to the valve housing and located downstream of the resuscitation bag and operable to release gas from the gas flow path at a first predetermined pressure differential between the path and ambient; and
    wherein the first safety release valve is located downstream of the check valve.

* * * * *